United States Patent [19]

Carney

[11] Patent Number: 5,569,262

[45] Date of Patent: Oct. 29, 1996

[54] GUIDE TOOL FOR SURGICAL DEVICES

[76] Inventor: William P. Carney, 4 High Ridge La., Oyster Bay, N.Y. 11771

[21] Appl. No.: 444,937

[22] Filed: May 19, 1995

[51] Int. Cl.⁶ .................................................. A61B 17/58
[52] U.S. Cl. ................................ 606/96; 606/86; 606/99; 606/53
[58] Field of Search ................................. 606/1, 53, 86, 606/96, 99

[56]  References Cited

U.S. PATENT DOCUMENTS

| 4,381,770 | 5/1983 | Neufeld | 128/92 BA |
| 4,621,630 | 11/1986 | Kenna | 128/922 VD |
| 4,708,139 | 11/1987 | Dunbar | 128/305.1 |
| 4,834,080 | 5/1989 | Brown | 128/92 VP |
| 4,911,153 | 5/1990 | Border | 606/98 |
| 4,945,904 | 8/1990 | Bolton et al. | 606/96 |
| 5,030,219 | 7/1991 | Matsen, III et al. | 606/86 |
| 5,100,408 | 3/1992 | Lackey | 606/79 |
| 5,312,408 | 5/1994 | Brown | 606/96 |
| 5,320,625 | 6/1994 | Bertin | 606/91 |

*Primary Examiner*—Michael Powell Buiz
*Assistant Examiner*—Mark S. Leonardo
*Attorney, Agent, or Firm*—Charles E. Temko

[57]  ABSTRACT

A guide tool for directing a surgical device into attachment with a bone segment includes a tubular portion having an axial bore extending from a proximal end to a distal end thereof for guiding the surgical device therethrough. A transversely extending pressure plate is affixed to the tubular portion at its distal end for applying finger pressure thereon to stabilize the bone segment while the surgical device is guided through the axial bore into attachment with the bone segment. The guide tool protects a surgeon's fingers from the surgical device and from the jagged surface of the bone segment.

10 Claims, 8 Drawing Sheets

GUIDE TOOL FOR SURGICAL DEVICES

BACKGROUND OF THE INVENTION

1. Field of the Invention

This invention relates generally to surgical instruments and more particularly to a guide tool for directing a surgical device into attachment with a bone segment.

2. Description of Related Art

Orthopedic surgical procedures often require that sharp pointed devices such as corkscrews, drills, nails, saws and other instruments be screwed or driven into a patient's skeletal structure. Hemiarthroplasty and total hip replacement operations are typical surgeries which involve driving a surgical device into a bone segment. As will be described in more detail below, there is a need during such procedures for a tool which not only offers the surgeon a means by which to guide the pointed device into engagement with the selected bone segment but also provides a means by which to protect his or her fingers during the process.

The following United States Patents represent a selective sample taken from a large number of prior art patents disclosing tools that are used as guides for pointed surgical devices during orthopedic procedures.

U.S. Pat. No. 4,621,630, which issued on Nov. 11, 1986 to Robert V. Kenna, discloses a guide used to saw cut the femoral neck at an angle of 45 degrees to the long shaft axis of the femur during a hip replacement procedure. This patent solves the problem of guiding the saw but does not address the problems associated with protecting the surgeon's fingers while stabilizing a movable femoral neck during the process of threading a corkscrew into it as part of the procedure for removing the femoral head from the acetabular socket after the saw cut has been made.

U.S. Pat. No. 4,911,153 which issued on Mar. 27, 1990 to Robert Border, discloses an orthopedic instrument which is secured to an intramedullary nail and which serves as an adjustable guide for drills, reamers, fasteners and other orthopedic devices. The disclosed instrument is not applicable to surgeries such as either a hemiarthroplasty procedure or a total hip replacement operation. During these procedures, there is a need for a tool to be used as a guide for a corkscrew employed to remove the femoral head from the acetabulum.

As can be seen from the foregoing, there exists a definite need for a tool that enables the surgeon to stabilize a movable bone segment during any surgical procedure which requires the attachment of a surgical device to a bone segment. Also, a guide tool is required which protects the surgeon's fingers while the device is being driven into the bone segment. In addition, a tool is needed which comprises a minimum number of components, that is easy for the surgeon to use and which provides an efficient method by which to obtain optimum attachment of the surgical device with the bone segment. Further, a tool is required which will accommodate various fracture angles that occur as a result of the accidental breaking of bones and which are encountered during certain surgical procedures performed to reduce these fractures.

SUMMARY OF THE INVENTION

The present invention overcomes the above described problems and disadvantages of the prior art and provides a novel guide tool for directing a surgical device into attachment with a bone segment.

According to a first embodiment of the present invention, the guide tool comprises a generally tubular portion forming a wall having an outside surface and an inside surface. The inside surface defines an axial bore extending between a proximal end and a distal end of the tubular portion and is shaped to receive and guide the surgical device therethrough. A transversely extending generally planar pressure plate and means for affixing the pressure plate to the tubular portion are formed at the distal end of the tubular portion. The pressure plate has a top side and a bottom side. The bottom side defines engagement means for securing the pressure plate to the bone segment and the top side defines a substantially planar surface for applying finger pressure thereon to urge the engagement means into securement with the bone segment.

According to a second embodiment, the means for affixing the pressure plate to the tubular portion include a slot formed in the pressure plate and an annular ring formed on the outside surface of the tubular portion at the distal end thereof. The slot defines transversely extending parallel sides which cooperate with the outside surface of the tubular portion so that the pressure plate is free to slide axially on the tubular portion and be manipulated angularly with respect thereto but is prevented from disengaging at the distal end therefrom by the annular ring.

According to a third embodiment, the means for affixing the pressure plate to the tubular portion include a centrally disposed axial bore formed in the pressure plate therethrough for receiving the tubular portion therein so that the tubular portion is free to pivot with respect to the pressure plate. The pressure plate defines first and second transversely extending pivot bores therethrough. The wall of the tubular member has first and second transversely extending trunion bores therein at the distal end thereof. The transversely extending bores are in alignment. First and second cylindrically shaped trunion pins are adapted to pivotally connect, respectively, the first pivot bore to the first trunion bore and the second pivot bore to the second trunion bore so that the pressure plate is pivotally affixed to the tubular portion.

DETAILED DESCRIPTION OF THE INVENTION

Before describing the details of the embodiments of the present invention, a discussion of prior art procedures is considered apposite.

Figure 1:
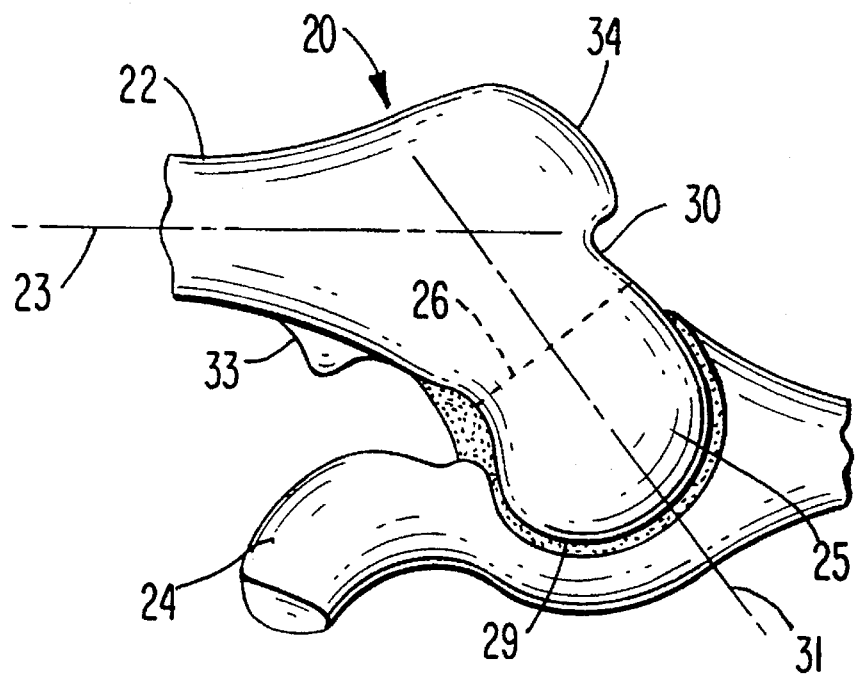
FIG. 1 is a simplified sectional view of a human hip, common in the prior art, showing the major bones of the hip joint.

Turning now to the figures, there is shown in FIG. 1, by way of explanation and to define terminology used herein, a simplified coronal cross section of a human hip joint generally referred to by reference character 20. The coronal section (viewed from the front of the body) in FIG. 1 is oriented to illustrate the relative positions of the components of the hip when a patient is lying on his or her side prepared for hip surgery. The femur 22 extends from the pelvis 24 to the knee (not shown) along the long axis 23 of the femur 22. The femur 22 articulates with the pelvis 24 through a spherically shaped bone structure formed at the top of the femur called the femoral head 25. The femoral head 25 fits into a socket in the pelvis known as the acetabulum or acetabular socket 29. An oblique section of bone, the femoral neck 30, connects the femur 22, to the femoral head 25. At the junction of the femoral neck 30 and the femur 22, there are two bone protrusions, the greater trochanter 34 and the lesser trochanter 33, which attach certain leg muscles to the femur 22. Hemiarthroplasty operations are generally performed on patients with femoral neck fractures and total hip replacement operations are performed on patients suffering from arthritic deterioration of the femoral head 25 and/or arthritic deterioration of the acetabulum 29. The surgical procedures for each of these operations are similar and have several steps in common.

It is well known that in both of the aforementioned procedures, the femoral head 25 is surgically removed or dislocated from its associated acetabular socket 29. It is also well known that as part of both of the aforementioned procedures, the femoral head 25 is replaced by a prosthesis having a spherical metallic end portion which is affixed to the top of the femur 22 and assembled into the acetabular socket 29. The following is a brief description of the surgical steps used to surgically dislocate the femoral head 25 from the acetabulum 29 prior to replacing the femoral head 25 with a prosthesis. Also, included is a brief description of the problems encountered by the surgeon during the dislocation of the femoral head 25 from its associated acetabular socket 29.

Hemiarthroplasties and total hip replacements are generally performed with the patient lying on his or her side. After the patient is properly anesthetized, scrubbed and draped, each procedure is started by making an incision into the outside aspect of the patient's hip 20 with tissue dissection carried down to the femoral neck 30. Typically, in the total hip replacement procedure, the femoral neck 30 is intact and the femoral head 25 and the acetabulum 29 have arthritic deterioration. In the hemiarthroplasty procedure, the femoral neck 30 has been fractured at a random angle with respect to its longitudinal axis 31 and separated from the femoral head 25 and the femoral head 25 and its associated acetabular socket 29 are anatomically normal. In both procedures, the femoral head 25 is dislocated and removed from the acetabular socket 29 by the surgeon.

To prepare the femoral head 25 for removal during the total hip procedure, the femoral neck 30 is separated from the femoral head 25 by means of a saw cut 26 made at an angle of approximately 45 degrees to the long axis 23 of the femur 22 in a plane substantially normal to the longitudinal axis 31 of the femoral neck 30 going through the femoral neck 30 at a level one to two finger breadths above the lesser trochanter 33. As previously mentioned, during the hemiarthroplasty procedure the femoral neck 30 has already been fractured and separated from the femoral head 25 and it is, therefore, not necessary to saw cut that portion of the femoral neck which remains attached to the femoral head 25.

Figure 2:
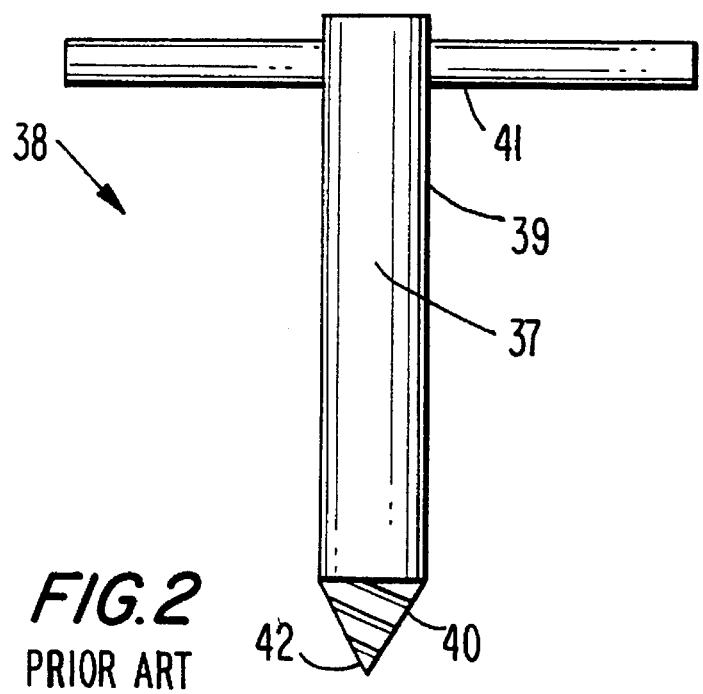
FIG. 2 pictures an orthopedic surgical corkscrew common in the prior art.
Figure 3:
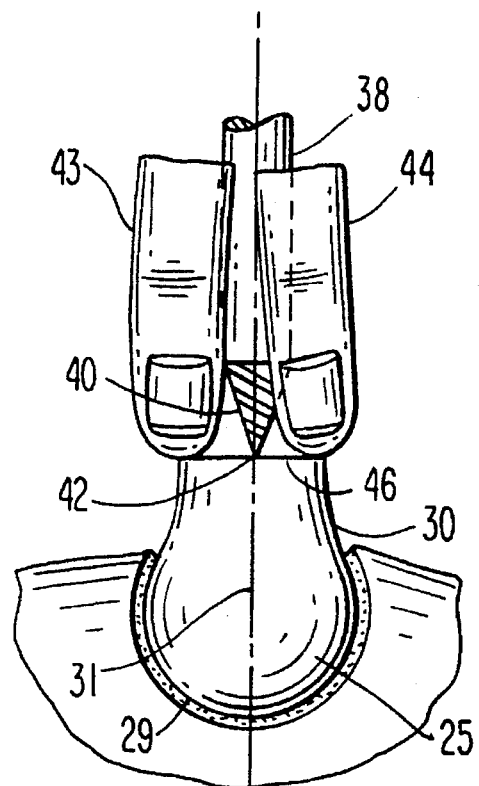
FIG. 3 illustrates a procedure, common in the prior art, for using the corkscrew pictured in FIG. 2.
Figure 4:
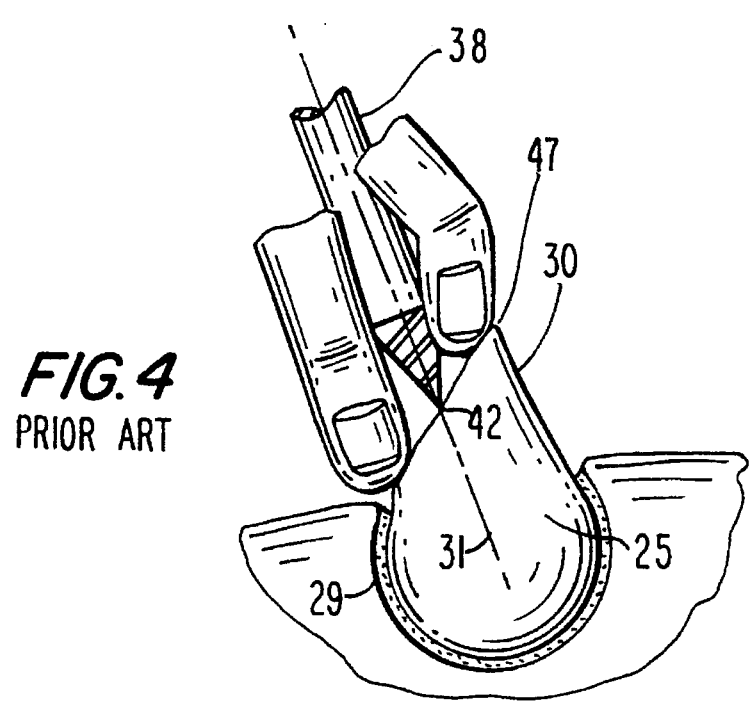
FIG. 4 illustrates an alternate procedure, common in the prior art, for using the corkscrew pictured in FIG. 2.

At this point in both cases, the surgeon is faced with the problem of removing the femoral head 25 from the acetabulum 29. The femoral head 25 is secured in its associated acetabular socket 29 by a close ball and socket fit which creates a strong retaining suction as the femoral head 25 is dislocated from the acetabulum 29. Because a relatively large withdrawal force is required to overcome this retaining force, the surgeon uses a surgical device, as shown in FIG. 2, typically referred to as a corkscrew, to assist in the removal procedure. The preferred corkscrew 38 comprises a stainless steel rod 39 having a longitudinal axis 37 with a self tapping screw thread 40 having a point 42 at one end and a grip or a handle 41 at the other. The corkscrew 38 is attached to the femoral head 28, as shown in FIG. 3, during a hip surgery as follows:

A right handed surgeon places the index finger 43 and middle finger 44 of his or her gloved left hand into the incision and contacts the severed surface 46 of the femoral neck 30 which remains attached to the femoral head 25. This is done to rotate the femoral head to an optimum access position and to hold it steady while the surgeon uses his or her gloved right hand (not shown) to manipulate the handle 41 (FIG. 2) of the corkscrew 38 to threadedly engage the self tapping screw 40 into the approximate center of the remaining portion of the femoral neck 30. Ideally, the self tapping screw 40 is driven into the femoral neck 30 along the longitudinal axis 31 of the femoral neck 30. This part of the operation is difficult and time consuming since the remaining portion of the femoral neck 30 may have a jagged surface 47 resulting from a fracture of the femoral neck 30, as shown in FIG. 4. Also, the remaining portion of the femoral neck 30 is free to rotate and rock because it is attached to the femoral head 25 which articulates in the acetabulum 29. The corkscrew insertion procedure is further+complicated because the surgeon is working in a blind hole and is concerned about puncturing his or her fingertips on the sharp edges which remain as part of the surface of the femoral neck 30 and/or puncturing his or her fingers with the pointed end 42 of the corkscrew 38. Once the corkscrew 38 is securely threaded into the femoral head 25, the surgeon uses the corkscrew 38 to remove the femoral head 25 from the acetabular socket 29.

Figure 5:
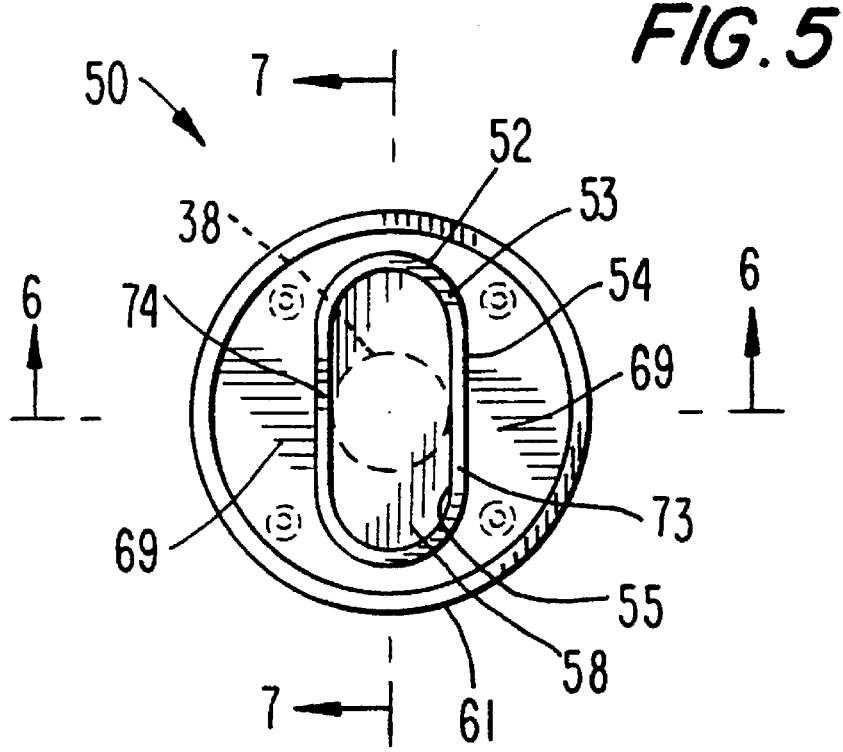
FIG. 5 is a plan view of the guide tool of the first embodiment of the present invention.
Figure 6:
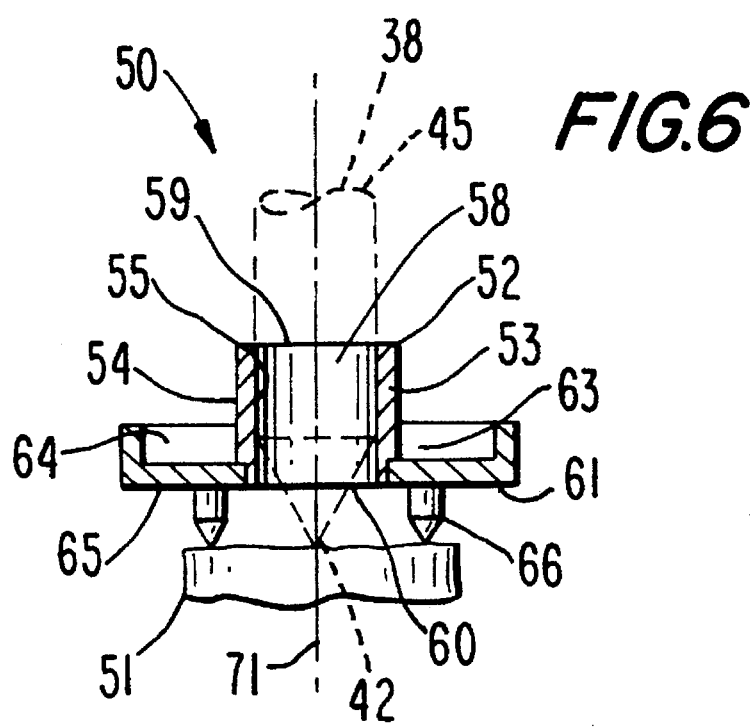
FIG. 6 is a sectional view of the guide tool taken along line 6—6 of FIG. 5.

Turning now to FIG. 5 and FIG. 6, there is illustrated a first embodiment of the present invention, a guide tool for surgical devices, indicated by reference character 50. The guide tool 50 comprises a generally tubular portion 52 forming a wall 53 having an outside surface 54 and an inside surface 55. An axial bore 58, defining transversely extending parallel sides 73 and 74, extends between a proximal end 59 and a distal end 60 of the tubular portion 52. The axial bore 58 is shaped to receive and guide therethrough, from its proximal end 59 to its distal end 60, a surgical device such as, but not limited to, a corkscrew 38 (represented hereinafter in the drawings by dotted lines).

At the distal end 60 of the tubular portion 52, there is formed a transversely extending pressure plate 61. The tubular portion 52 and the pressure plate 61 are preferably fabricated from a surgical grade of stainless steel. Any one of a number of manufacturing techniques may be used such as, but not limited to, numerically controlled milling to fabricate the guide tool 50 as, for example, one integral piece. Alternatively, the tubular portion 52 and the pressure plate 61 may be formed as two separate pieces and preferably welded together along a seam 63 defined at the interface between the distal end 60 of the tubular portion 52 and a top side 64 of the pressure plate 61. A plurality of generally cylindrical spike-like pins 66 is mounted on a bottom side 65 of the pressure plate 61 for securing a bone segment 51 to the pressure plate 61. The spike-like pins 66 are preferably fabricated from surgical grade stainless steel and affixed to the bottom side 65 of the pressure plate 61 by any one of a number of well known methods.

The top side 64 of the pressure plate 61 defines a substantially planar surface 69 for applying finger pressure thereon to urge the pressure plate 61 and its associated spike-like pins 66 into engagement with the bone segment 51. The surgical device 38 has a pointed end 42 and a grip end 45. As shown in FIG. 6, when the pointed end 42 extends below the distal end 60 of the axial bore 58 and contacts the bone segment 51, the grip end 45 extends above the proximal end 59 so that it may be manipulated by the surgeon to drive the pointed end 42 into attachment with the bone segment 51 preferably along a longitudinal axis 71 of the bone segment 51.

Figure 7:
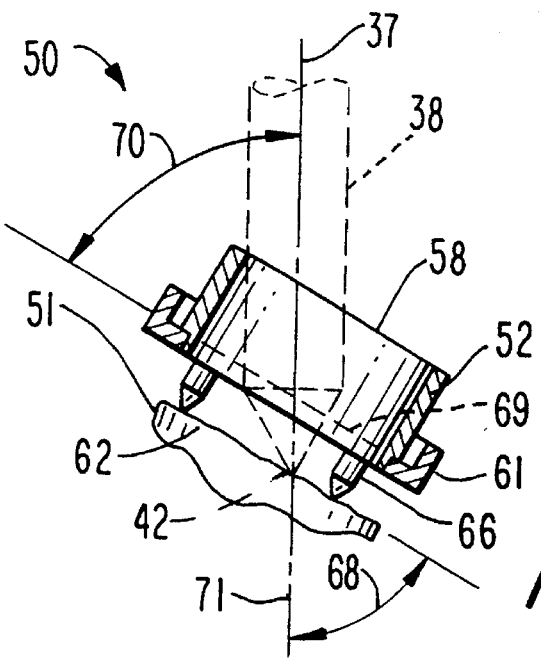
FIG. 7 is a sectional view of the guide tool taken along line 7—7 of FIG. 5 showing the pressure plate angularly rotated with respect to the longitudinal axis of the corkscrew.

FIG. 7 pictures the guide tool 50 angularly rotated with respect to the longitudinal axis 37 of the surgical device 38. In this position, the pressure plate 61 is spatially disposed to secure the bone segment 51 which, as shown in FIG. 7, has been accidentally fractured at an angle 68 relative to its longitudinal axis 71. The axial bore 58 of the tubular portion 52 receives the surgical device 38 at an aiming angle 70 formed between the planar surface 69 of the pressure plate 61 and the longitudinal axis 37 of the surgical device 38. The parallel sides 73 and 74 (FIG. 5) of the axial bore 58 cooperate with the surgical device 38 to guide its pointed end 42 into attachment with the angularly disposed surface 62 of the bone segment 51.

Figure 8:
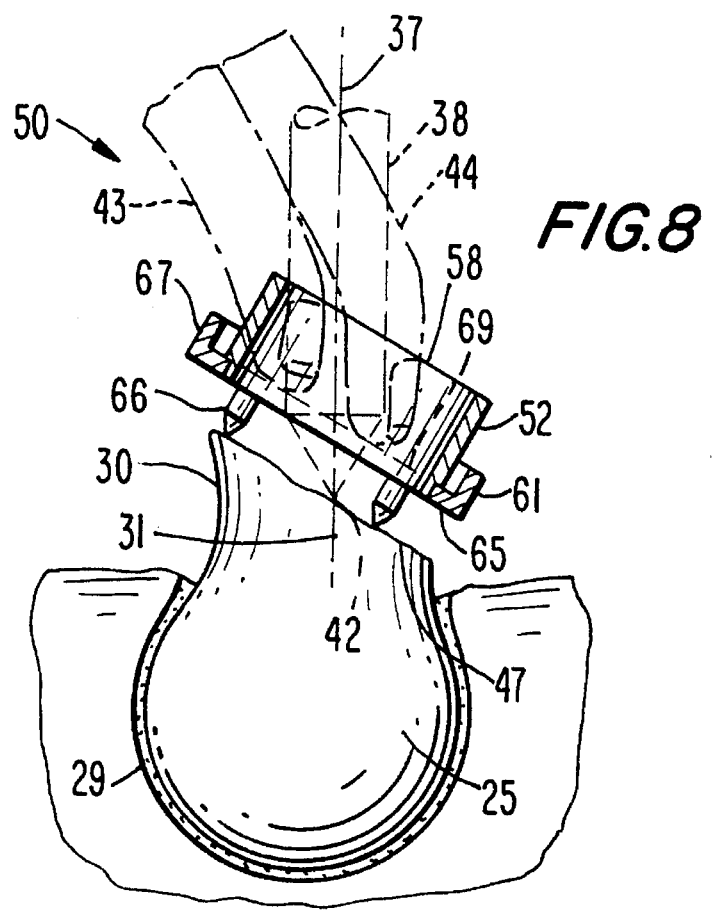
FIG. 8 illustrates the use of the guide tool of the first embodiment during a hip surgery procedure.
Figure 9:
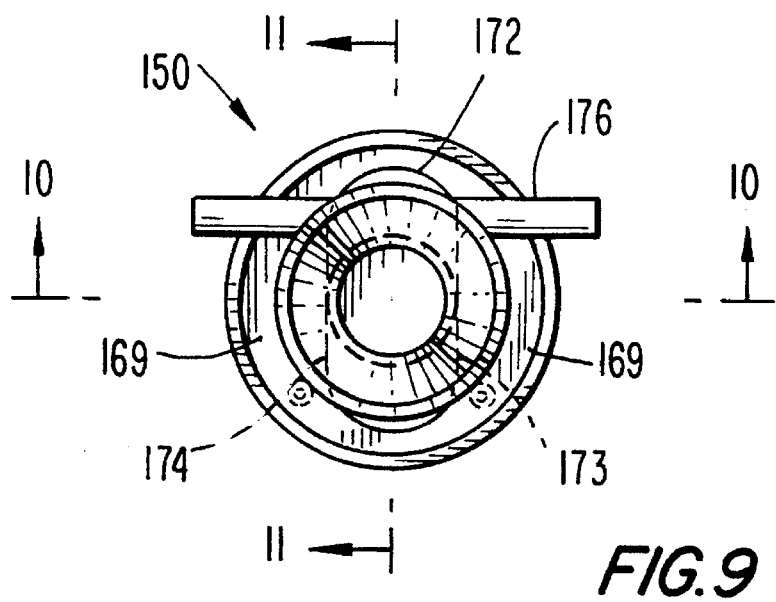
FIG. 9 is a plan view of the guide tool of the second embodiment of the present invention.
Figure 10:
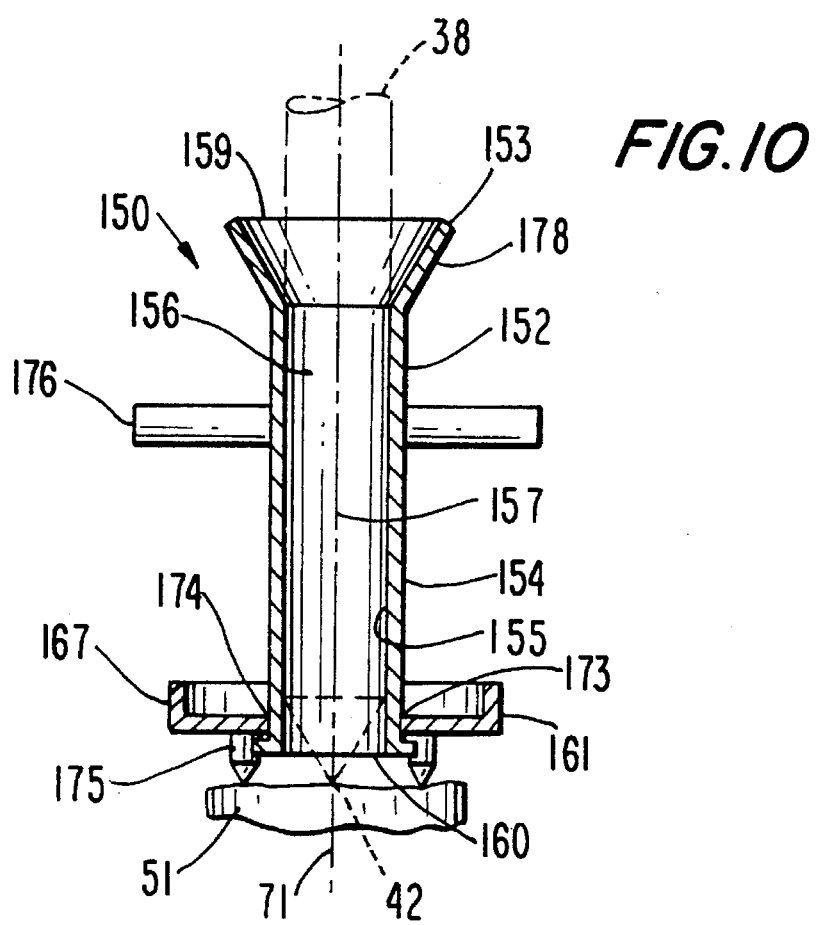
FIG. 10 is a sectional view of the guide tool taken along line 10—10 of FIG. 9.

FIG. 8 shows the surgeon's fingers (represented hereinafter in the drawings by dotted lines) positioned on the guide tool 50 delineating the use of the first embodiment of the present invention for removing the femoral head 25 and the attached portion of the severed femoral neck 30 from the associated acetabular socket 29 during hip surgery. After making an incision to expose the femoral neck 30, and after preparing the femoral neck 30 for removal from its associated acetabular socket 29, the surgeon positions the guide tool 50 on either the saw cut surface 46 (FIG. 3) or the fractured surface 47 of the femoral neck 30. A right handed surgeon places the index finger 43 and the middle finger 44 of his or her gloved left hand on the planar surface 69 of the pressure plate 61 and applies pressure thereon to secure the severed femoral neck 30 to the spike-like pins 66 affixed to the bottom side 65 of the pressure plate 61 so that the axial bore 58 is in optimum alignment with the axis 31 of the femoral neck 30. The surgeon then inserts the corkscrew 38 into the axial bore 58 so that its axis 37 is substantially aligned with the longitudinal axis 31 of the femoral neck 30. Once the corkscrew 38 is aligned, the surgeon manipulates the handle 41 (FIG. 2) of the corkscrew 38 with his or her right hand (not shown) to threadedly attach the corkscrew 38 to the femoral neck 30 while finger pressure is being applied to the pressure plate 61 to stabilize the femoral head 25. After optimum threaded attachment is achieved, the surgeon employs the corkscrew 38 to remove the femoral head 25 from its associated acetabular socket 29.

As can be seen in FIG. 8, the tubular portion 52 protects the surgeon's fingers 43 and 44 from the pointed end 42 of the corkscrew 38, the planar surface 69 isolates his or her fingers from contacting the jagged surface 47 of the femoral neck 30 and an annular rim 67, formed on the periphery of the pressure plate 61, prevents the surgeon's fingers 43 and 44 from slipping off the planar surface 69.

Turning now to FIG. 9 through FIG. 12 in the drawings, there is illustrated a second embodiment of the present invention offering certain variations over the first embodiment. Principally, the tubular portion is elongated to receive and enclose a longer axial length of the surgical device than is received and enclosed by the tubular portion of the first embodiment. Further, in the second embodiment, the tubular portion and the pressure plate are formed as separate pieces so that the pressure plate is free to slide axially and rotate angularly with respect to the tubular portion. In addition, the tubular portion may be formed with a funnel shaped mouth at its proximal end for guiding the surgical device into its axial bore. The advantage of this construction is that the longer tubular member and the funnel shaped mouth prevent the surgical device from contacting the surgeon's fingers for substantially the entire length of the surgeon's fingers.

Referring to FIG. 9 through FIG. 12 in the drawings, the second embodiment of the present invention is generally referred to by reference character 150. To avoid needless repetition, certain of the component parts of the second embodiment have been designated by reference characters corresponding to those employed in FIG. 1 through FIG. 8 describing the first embodiment with the additional prefix "1".

The second embodiment comprises a generally tubular portion 152 forming a wall 153 having an outside surface 154 and an inside surface 155. An axial bore 156 having an axis 157 extends between a proximal end 159 and a distal end 160 of the tubular portion 152. The axial bore 156 is shaped to receive and guide therethrough, from its proximal end 159 to its distal end 160, a surgical device such as, but not limited to, a corkscrew 38.

At the distal end 160 of the tubular portion 152, there is located a transversely extending pressure plate 161. As previously described, the pressure plate 161 and the tubular portion 152 are preferably fabricated from surgical grade stainless steel by well known manufacturing techniques. In the second embodiment 150, the tubular portion 152 and the pressure plate 161 are manufactured as separate pieces. The pressure plate 161 has formed therein a slot 172 which interacts with an annular ring 175 formed on the outside surface 154 of the tubular portion 152 at the distal end 160 thereof. The slot 172 defines transversely extending parallel sides 173 and 174 which cooperate with the outside surface 154 of the tubular portion so that the pressure plate 161 is free to slide axially on the tubular portion 152. The pressure plate 161 may also be rotated angularly with respect to the tubular portion 152 but is prevented from sliding off the distal end 160 thereof by the annular ring 175 formed thereon.

Figure 11:
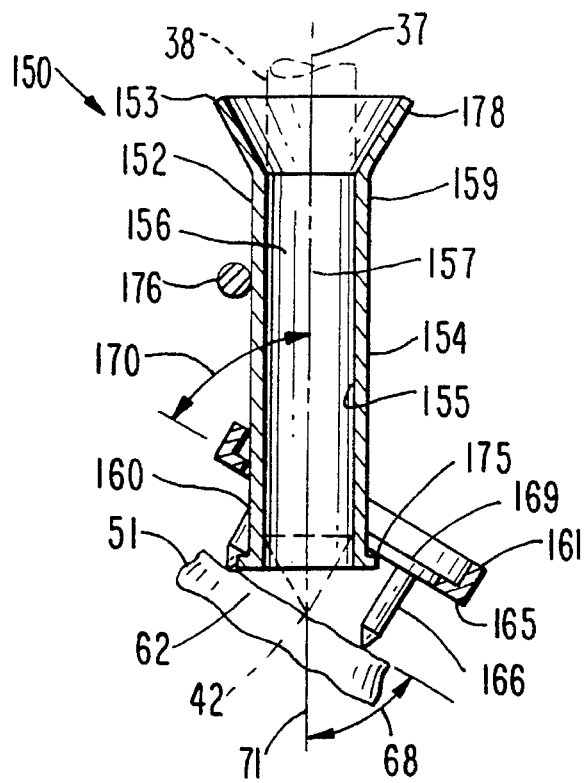
FIG. 11 is a sectional view of the guide tool taken along line 11—11 of FIG. 9 showing the pressure plate angularly rotated with respect to the axis of the tubular portion.

FIG. 11 pictures the pressure plate 161 angularly rotated with respect to the longitudinal axis 157 of the axial bore 156 of the tubular portion 152. In this position, the pressure plate 161 is spatially disposed to secure the bone segment 51 which, as shown in FIG. 11, has been accidentally fractured at an angle 68 relative to its longitudinal axis 71. A funnel shaped mouth 178 formed at the proximal end 159 of the tubular portion 152 receives the pointed end 42 of the surgical device 38 into the axial bore 156 which is disposed at an aiming angle 170 formed between the planar surface 169 of the pressure plate 161 and the longitudinal axis 157 of the axial bore 156. The parallel sides 173 and 174 (FIG. 9) cooperated with the outside surface 154 of the tubular portion 152 to accommodate the aiming angle 170 while preventing the pressure plate 161 from disengaging from the distal end 160 of the tubular portion 152 because of the annular ring 175 formed thereon.

Figure 12:
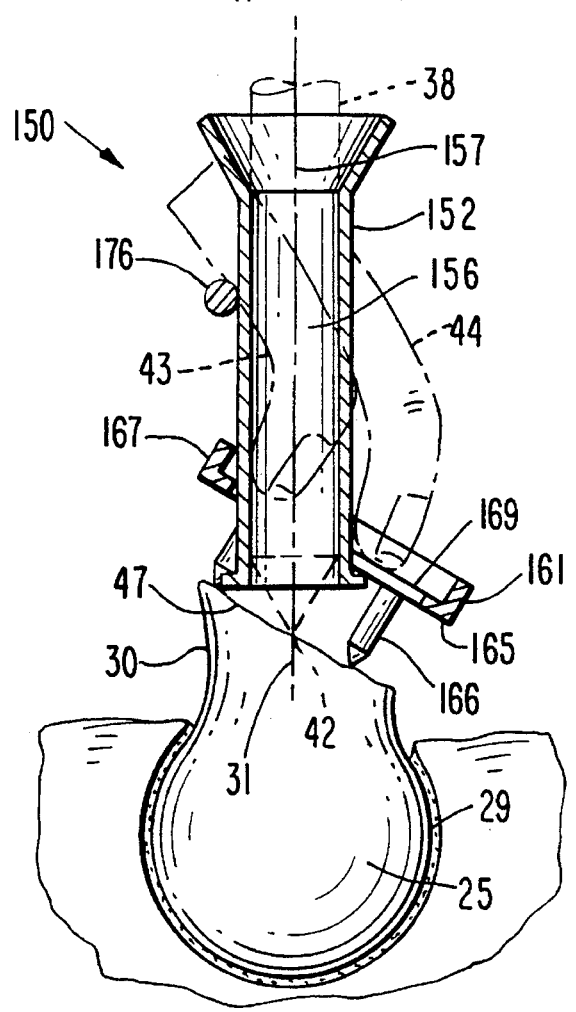
FIG. 12 illustrates the use of the guide tool of the second embodiment during a hip surgery procedure.
Figure 13:
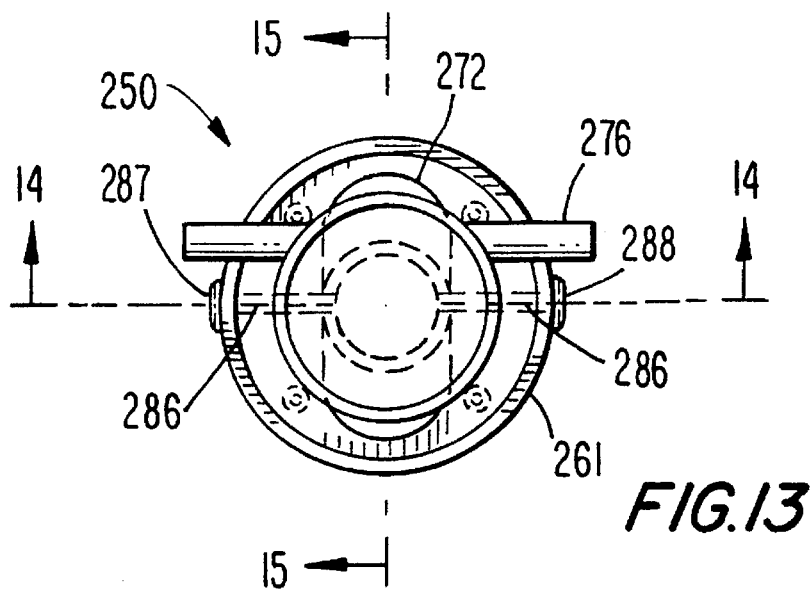
FIG. 13 is a plan view of the guide tool of the third embodiment of the present invention.

FIG. 12 shows the surgeon's fingers positioned on the guide tool 150 delineating the use of the second embodiment of the present invention during hip surgery. As previously described, after preparing the femoral neck 30, the surgeon positions the guide tool 150 on either the saw cut surface 46 (FIG. 3) or the fractured surface 47 of the femoral neck 30. A right handed surgeon places the index finger 43 and the middle finger 44 of his or her gloved left hand on the planar surface 169 of the pressure plate 161 and applies pressure thereon to secure the severed femoral neck 30 to the spikelike pins 166 affixed to the bottom side 165 of the pressure plate 161. The surgeon manipulates the tubular portion 152 so that the axis 157 of its axial bore 156 is aimed along the axis 31 of the femoral neck 30. A transversely extending guide rod 176, affixed to the tubular portion 152, may be employed by the surgeon to assist in manipulating and holding the tubular portion 152. Once aligned, the surgeon inserts the corkscrew 38 into the axial bore 156 and manipulates the handle 41 (FIG. 2) of the corkscrew 38 with his or her right hand (not shown) to drive the corkscrew 38 into threaded attachment with the femoral neck 30 while stabilizing the femoral neck 30 with finger pressure applied to the pressure plate 161. After optimum threaded attachment is achieved, the surgeon manipulates the corkscrew 38 to remove the femoral head 25 from its acetabular socket 29.

As can be seen in FIG. 12, the tubular portion 152 protects the surgeon's fingers, 43 and 44, from being punctured by the pointed end 42 of the corkscrew 38 for substantially the entire length of his or her fingers, 43 and 44. Further, the pressure plate 161 isolates his or her fingers, 43 and 44, from contacting the jagged surface 47 of the femoral neck 30 and an annular rim 167, formed on the periphery of the pressure plate 161, prevents the surgeon's fingers, 43 and 44, from slipping off the planar surface 169.

Turning now to FIG. 13 through FIG. 16 in the drawings, there is illustrated a third embodiment of the present invention offering certain variations over the first two embodiments. In the third embodiment, the elongated tubular portion is pivotally attached to the pressure plate such that the pressure plate is free to pivot about a transversely extending pivot axis defined at the distal end of the tubular portion. One of the advantages of this construction is that the tubular portion is pivotally interconnected to the pressure plate thereby facilitating aiming the bore of the tubular portion while maintaining finger pressure on the pressure plate to secure the bone segment.

Referring to FIG. 13 through FIG. 16 in the drawings, the third embodiment of the present invention is generally referred to by reference character 250. To avoid needless repetition, certain of the component parts of the third embodiment have been designated by reference characters corresponding to those employed in FIG. 1 through FIG. 8 describing the first embodiment with the additional prefix "2".

The third embodiment comprises a generally tubular portion 252 forming a wall 253 having an outside surface 254 and an inside surface 255. An axial bore 256 having an axis 257 extends between a proximal end 259 and a distal end 260 of the tubular portion 252. The axial bore 256 is shaped to receive and guide therethrough, from its proximal end 259 to its distal end 260, a surgical device such as, but not limited to, a corkscrew 38.

Figure 14:
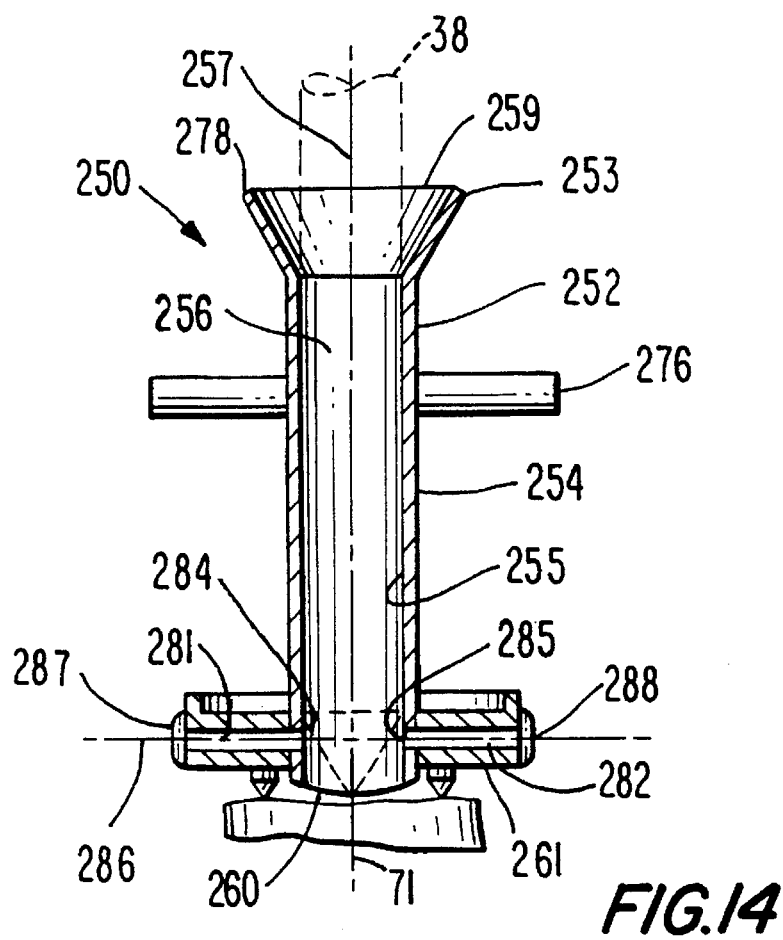
FIG. 14 is a sectional view of the guide tool taken along line 14—14 of FIG. 13.

As previously described, at the distal end 260 of the tubular portion 252, there is located a transversely extending pressure plate 261. In the third embodiment, both the tubular portion 252 and the pressure plate 261 are preferably formed from a surgical grade of stainless stainless steel as delineated above. The pressure plate 261 has formed therethrough a centrally disposed axial bore 272 adapted to receive therein the tubular portion 252 so that the tubular portion 252 is free to rotate angularly with respect to the pressure plate 261. There are also formed in the pressure plate 261 laterally extending first 281 and second 282 pivot bores communicating with, respectively, first 284 and second 285 trunion bores formed in the distal end 260 of the tubular portion 252. As shown in FIG. 14, the axes of the transversely extending pivot bores, 281 and 282, and the axes of the transversely extending trunion bores, 284 and 285, are aligned along a transversely extending common pivot axis 286. Cylindrically shaped first and second trunion pins, 287 and 288, preferably fabricated from surgical grade stainless steel, pivotally interconnect, respectively, the first pivot bore 281 to the first trunion bore 284 and the second pivot bore 282 to the second trunion bore 285 so that the pressure plate 261 is pivotally connected to the tubular portion 252 about the pivot axis 286.

Figure 15:
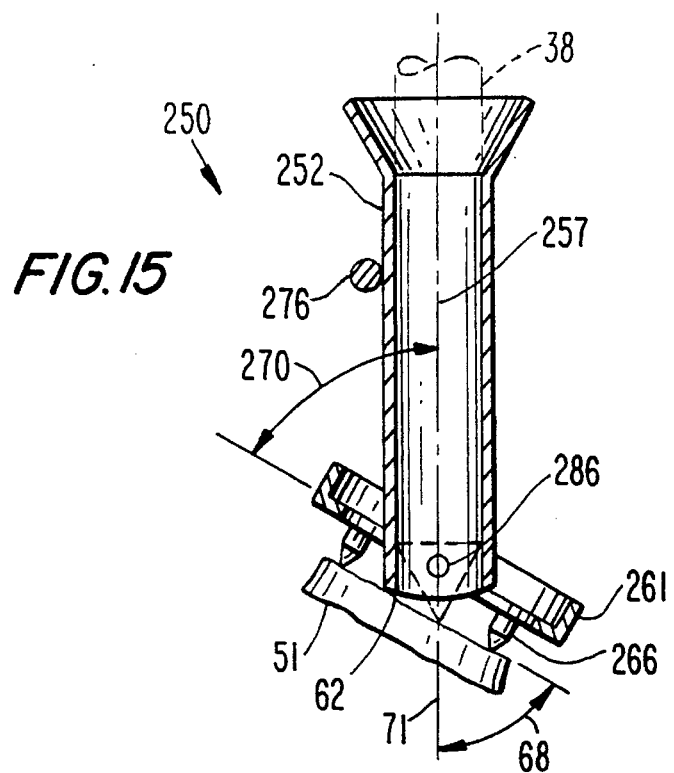
FIG. 15 is a sectional view of the guide tool taken along line 15—15 of FIG. 13 showing the pressure plated angularly pivoted with respect to the longitudinal axis of the tubular portion.

FIG. 15 pictures the pressure plate 261 angularly rotated about the pivot axis 286 with respect to the tubular portion 252. The pressure plate 261 in the third embodiment 250 secures the bone segment 51 in substantially the same way as the bone segment 51 is secured by the pressure plates 61 and 161 of the first and second embodiments as described above.

Figure 16:
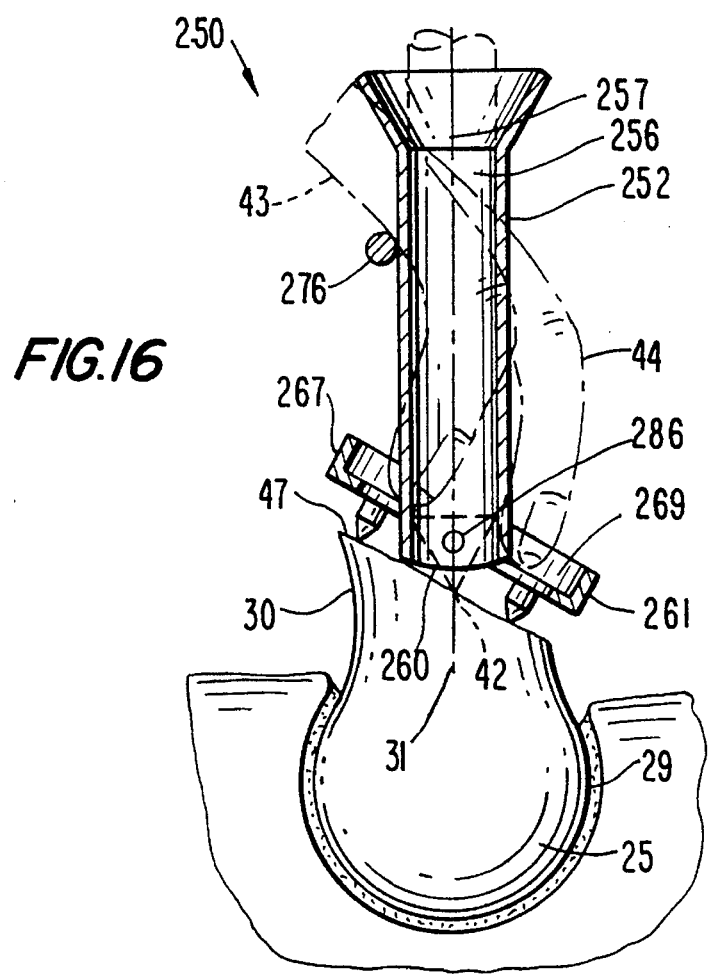
FIG. 16 illustrates the use of the guide tool of the third embodiment during a hip surgery procedure.

FIG. 16 shows the surgeon's fingers, 43 and 44, positioned on the guide tool 250 delineating the use of the third embodiment during hip surgery. The guide tool 250 is employed in substantially the same manner as the guide tool 150 of the second embodiment as described above. The tubular portion 252 is pivotally connected to the distal end 260 of the tubular portion 252 about the pivot axis 286 thereby facilitating aiming the axis 257 of the bore 256 in alignment with the longitudinal axis 31 of the femoral neck 30.

It is to be understood that the present invention is not limited to the precise details of the structure shown and set forth in this specification, for obvious modifications will occur to those skilled in the art to which the invention pertains.

What is claimed is:

1. A guide tool for directing a surgical device into attachment with a bone segment comprising:

a generally tubular portion forming a wall having an outside surface and an inside surface, said inside surface defining an axial bore extending between a proximal end and a distal end of said tubular portion, said axial bore being shaped for receiving and guiding said surgical device therethrough;

a transversely extending generally planar pressure plate and means for affixing said pressure plate to said tubular portion formed at said distal end thereof; and said pressure plate forming a top side and a bottom side, said bottom side defining engagement means for securing said pressure plate to said bone segment, said top side defining a substantially planar surface for applying finger pressure thereon to urge said engagement means into securement with said bone segment.

2. A guide tool in accordance with claim 1 wherein said means for affixing said pressure plate to said tubular portion include a slot formed in said pressure plate and an annular ring formed on said outside surface of said tubular portion at said distal end thereof, said slot defining transversely extending parallel sides, said parallel sides cooperating with said outside surface of said tubular portion so that said pressure plate is free to slide axially on said tubular portion and be manipulated angularly with respect thereto but is prevented from disengaging at said distal end therefrom by said annular ring.

3. A guide tool in accordance with claim 1 wherein said means for affixing said pressure plate to said tubular portion include a centrally disposed axial bore formed in said pressure plate therethrough for receiving said tubular portion therein so that said tubular portion is free to pivot with respect to said pressure plate, said pressure plate defining first and second transversely extending pivot bores therethrough, said wall of said tubular member having first and second transversely extending trunion bores therein at said distal end thereof, said transversely extending bores being in alignment, first and second cylindrically shaped trunion pins, said first trunion pin being adapted to pivotally connect said first pivot bore to said first trunion bore and said second trunion pin being adapted to pivotally connect said second pivot bore to said second trunion bore so that said pressure plate is pivotally affixed to said tubular portion.

4. A guide tool in accordance with claim 1 wherein said pressure plate includes an annular rim formed on an outside edge thereof to prevent the fingers of a surgeon from sliding off said pressure plate.

5. A guide tool in accordance with claim 1 wherein said means for securing said pressure plate to said bone segment includes at least one spike-like member.

6. A guide tool in accordance with claim 1 wherein said tubular portion includes a transversely extending guide rod affixed thereto.

7. A guide tool in accordance with claim 1 wherein said tubular portion includes a funnel shaped mouth at said proximal end thereof.

8. A method for removing a femoral head and an attached portion of a severed femoral neck from an associated acetabular socket during a hip surgery using a surgical corkscrew and a guide tool, said guide tool including an axial bore for guiding said corkscrew and a pressure plate defining means for securing said severed femoral neck, said corkscrew having a self tapping screw end for threadedly attaching said femoral neck to said corkscrew and a handle end for manipulating said corkscrew, said method comprising the steps of:

positioning said guide tool on said attached portion of said femoral neck;

applying finger pressure to said pressure plate to secure said femoral neck;

aiming said axial bore of said guide tool along said longitudinal axis of said severed femoral neck;

inserting said corkscrew into said axial bore;

driving said corkscrew into said femoral neck while securing said femoral neck with finger pressure applied to said pressure plate; and manipulating said corkscrew to remove said femoral head and said attached portion of said femoral neck from said associated acetabular socket.

9. A guide tool for directing a surgical device into attachment with a bone segment comprising: a generally tubular portion forming a wall having an outside surface and an inside surface, said inside surface defining an axial bore extending between a proximal end and a distal end of said tubular portion, said axial bore being shaped for receiving and guiding said surgical device therethrough; a transversely extending generally planar pressure plate and means for affixing said pressure plate to said tubular portion formed at said distal end thereof; and said pressure plate forming a top side and a bottom side, said bottom side defining engagement means for securing said pressure plate to said bone segment, said top side defining a substantially planar surface for applying finger pressure thereon to urge said engagement means into securement with said bone segment; said means for affixing said pressure plate to said tubular portion include a centrally disposed axial bore formed in said pressure plate therethrough for receiving said tubular portion therein, so that said tubular portion is free to pivot with respect to said pressure plate, said pressure plate defining first and second transversely extending pivot bores therethrough, said wall of said tubular member having first and second transversely extending trunion bores therein at said distal end thereof, said transversely extending bores being in alignment; first and second cylindrically shaped trunion pins, said first trunion pin being adapted to pivotally contact said first pivot bore to said first trunion bore, and said second trunion pin being adapted to pivotally connect said second pivot bore to said second trunion bore, so that said pressure plate is pivotally affixed to said tubular portion.

10. A guide tool in accordance with claim 9, wherein said pressure plate includes an annular rim formed on an outside edge thereof to prevent the fingers of a surgeon from sliding off said pressure plate.

* * * * *